United States Patent
Dai (10) Patent No.: US 7,708,410 B2
(45) Date of Patent: May 4, 2010

(54) CORRECTION OF PRESBYOPIA USING ADAPTIVE OPTICS AND ASSOCIATED METHODS

(75) Inventor: Guangming Dai, Fremont, CA (US)

(73) Assignee: AMO Manufacturing USA, LLC, Santa Ana, CA (US)

( * ) Notice: Subject to any disclaimer, the term of this patent is extended or adjusted under 35 U.S.C. 154(b) by 0 days.

(21) Appl. No.: 12/124,116

(22) Filed: May 20, 2008

(65) Prior Publication Data
US 2008/0218693 A1    Sep. 11, 2008

Related U.S. Application Data (63) Continuation of application No. 10/872,331, filed on Jun. 17, 2004, now Pat. No. 7,387,387.

(51) Int. Cl.
  *A61B 3/02* (2006.01)
  *A61B 3/14* (2006.01)
(52) U.S. Cl. .................. 351/239; 351/206
(58) Field of Classification Search .......... 351/200–246
See application file for complete search history.

(56) References Cited

U.S. PATENT DOCUMENTS

| | | | |
|---|---|---|---|
| 3,903,871 A | 9/1975 | Chisum et al. ............ 600/489 |
| 5,682,223 A | 10/1997 | Menezes et al. | |
| 5,684,560 A | 11/1997 | Roffman et al. | |
| 5,724,258 A | 3/1998 | Roffman | |
| 5,807,377 A | 9/1998 | Madhani et al. | |
| 6,050,687 A | 4/2000 | Bille et al. .................. 351/212 |
| 6,155,684 A | 12/2000 | Bille et al. .................. 351/212 |
| 6,200,342 B1 | 3/2001 | Tassignon | |
| 6,280,435 B1 | 8/2001 | Odrich et al. | |
| 6,554,429 B1 | 4/2003 | Campin et al. | |
| 6,679,606 B2 | 1/2004 | Campin et al. | |
| 6,682,196 B2 | 1/2004 | Sheets, Jr. et al. | |
| 7,002,688 B2 | 2/2006 | Aravanis et al. | |
| 7,431,455 B2 | 10/2008 | Chernyak .................. 351/205 |
| 2002/0135736 A1* | 9/2002 | Stark et al. ................. 351/211 |
| 2002/0140902 A1 | 10/2002 | Guirao et al. | |
| 2003/0025874 A1 | 2/2003 | Williams et al. | |
| 2003/0053026 A1 | 3/2003 | Roorda | |

(Continued)

FOREIGN PATENT DOCUMENTS

EP    1060703 A    12/2000

(Continued)

OTHER PUBLICATIONS

Loewenfeld, Irene., E., *The Pupil: Anatomy, Physiology and Clinical Applications*, vol. 1 (1993) Wayne State University Press, Detroit, MI, pp. 296:301-304.

(Continued)

*Primary Examiner*—Mohammed Hasan (57) ABSTRACT

Devices, systems, and methods measure, diagnose, and/or treat one or both eyes of a patient. Adaptive optics systems (such as those having a deformable mirror) may be configured to an aspherical or multi-spherical presbyopia-mitigating prescriptive shape to allow objective and/or subjective measurements of a candidate prescription. A plurality of viewing distances allow subjective and/or objective evaluations of performance using a light spot or a test viewing image. Measurements of aberrations at selected viewing conditions (including distances and/or brightness) with correlating pupil sizes may also be provided.

12 Claims, 8 Drawing Sheets

U.S. PATENT DOCUMENTS

| | | |
|---|---|---|
| 2003/0071967 A1 | 4/2003 | Campin et al. |
| 2003/0199858 A1 | 10/2003 | Schelonka |
| 2005/0024586 A1 | 2/2005 | Teiwes et al. |

FOREIGN PATENT DOCUMENTS

| | | |
|---|---|---|
| EP | 1138252 A | 10/2001 |
| EP | 1366706 A | 12/2003 |
| JP | 2003199712 A | 7/2003 |
| WO | WO01/21062 A | 3/2001 |
| WO | WO02/09579 A1 | 2/2002 |
| WO | WO03/009746 A | 2/2003 |

OTHER PUBLICATIONS

Moreira, et al. "Multifocal Corneal Topographic Changes with Excimer Laser Photorefractive Keratectomy", *Arch. Ophthalmol.* (1992) 110:994-999.

Vinciguerra, et al. "Excimer Laser Photorefractive Keratectomy for Presbyopia: 24 month Follow-up in Three Eyes", *Journal of Refractive Surgery* (1998) 14:31.

Wikipedia, "Adaptive Optics", http://en.wikipedia.org/wiki/Adaptive_optics,pp. 1-5.

EPO Supplementary Partial European Search Report, EP05762290, Sep. 24, 2007.

* cited by examiner

CORRECTION OF PRESBYOPIA USING ADAPTIVE OPTICS AND ASSOCIATED METHODS

CROSS-REFERENCES TO RELATED APPLICATIONS

This is a continuation patent application which claims priority from U.S. patent application Ser. No. 10/872,331 filed on Jun. 17, 2004, now U.S. Pat. No. 7,387,387 B2 the full disclosure of which is incorporated herein by reference.

BACKGROUND OF THE INVENTION

This invention relates to optical diagnosis and correction, and in particular provides methods, devices, and systems for treating presbyopia and other vision conditions, for evaluating and deriving prescriptions for treatment of presbyopia and other vision conditions, and/or for measuring the response of the eye to different viewing conditions.

Presbyopia is a condition that affects the accommodation properties of the eye. As objects move closer to a young, properly functioning eye, ciliary muscle contraction and zonular relaxation allow the lens of the eye to become rounder or more convex, and thus increase its optical power and ability to focus at near distances. Accommodation can allow the eye to focus and refocus between near and far objects.

Presbyopia normally develops as a person ages, and is associated with a natural progressive loss of accommodation, sometimes referred to as "old sight." The presbyopic eye often loses the ability to rapidly and easily refocus on objects at varying distances. There may also be a loss in the ability to focus on objects at near distances. Although the condition progresses over the lifetime of an individual, the effects of presbyopia usually become noticeable after the age of 45 years. By the age of 65 years, the crystalline lens has often lost almost all elastic properties and has only limited ability to change shape. Residual accommodation refers to the amount of accommodation that remains in the eye. A lower degree of residual accommodation contributes to more severe presbyopia, whereas a higher amount of residual accommodation correlates with less severe presbyopia.

Known methods and devices for treating presbyopia seek to provide vision approaching that of an emmetropic eye. In an emmetropic eye, both distant objects and near objects can be seen due to the accommodation properties of the eye. To address the vision problems associated with presbyopia, reading glasses have traditionally been used by individuals to add plus power diopter to the eye, thus allowing the eye to focus on near objects and maintain a clear image. This approach is similar to that of treating hyperopia, or farsightedness.

Presbyopia has also been treated with bi-focal eyeglasses, where one portion of the lens is corrected for distance vision, and another portion of the lens is corrected for near vision. When peering down through the bifocals, the individual looks through the portion of the lens corrected for near vision. When viewing distant objects, the individual looks higher, through the portion of the bi-focals corrected for distance vision. Thus with little or no accommodation, the individual can see both far and near objects.

Contact lenses and intra-ocular lenses (IOLs) have also been used to treat presbyopia. One approach is to provide the individual with monovision, where one eye (usually the primary eye) is corrected for distance-vision, while the other eye is corrected for near-vision. Unfortunately, with monovision the individual may not clearly see objects that are intermediately positioned because the object is out-of-focus for both eyes. Also, an individual may have trouble seeing with only one eye, or may be unable to tolerate an imbalance between their eyes. In addition to monovision, other approaches include bilateral correction with either bi-focal or multi-focal lenses. In the case of bi-focal lenses, the lens is made so that both a distant point and a near point can be focused. In the multi-focal case, there may exist many focal points between near targets and far targets.

In the field of refractive surgery, certain ablation profiles have been suggested to treat the condition, often with the goal of increasing the range of focus of the eye (rather than restoring accommodation in the patient's eye). Many of these ablation profiles can provide a single excellent focus of the eye, yet they do not provide an increased depth of focus such that optimal distance acuity, optimal near acuity, and acceptable intermediate acuity occur simultaneously. Shapes have been proposed for providing enhanced distance and near vision, yet current approaches do not provide ideal results for all patients.

Prior presbyopia treatment may generally be categorized into two approaches: passive and active. Active treatments generally seek to restore accommodation, such as through the use of an artificial accommodating intra-ocular lenses (IOLs), scleral expansion bands (SEBs), and drug therapies. Passive treatments generally seek to change the optical properties of the human eye to maintain an acceptable compromise between near vision and distance vision. Passive treatments include multifocal and bifocal contact lenses, IOLs, spectacle lenses, monovision, and the like. Effectiveness of both active and passive techniques has generally been established by human clinical trials which are time-consuming, expensive and may involve some risk for the involved patients. Optical modeling can provide significant insight into proposed techniques, but substantial uncertainties remain, including those associated with the retinal response and neural processing of the optical signals transmitted through the ocular optics.

In light of the above, it would be desirable to have improved methods, devices, and systems for treatment of presbyopia and other vision defects. It would also be desirable to have improved methods, devices, and systems for measuring the optical and/or visual response of the human viewing system and for developing new prescriptions to treat presbyopia and other viewing defects. It would generally be desirable to increase the percentage of the population which can be effectively treated for presbyopia and other vision defects without greatly increasing the cost, risk, and/or complexity of diagnosis and/or treatment over current techniques.

BRIEF SUMMARY OF THE INVENTION

The present invention generally provides improved devices, systems, and methods for measuring, diagnosing, and treating one or both eyes of a patient. The techniques of the present invention are particularly well-suited for addressing presbyopia and accommodation, and are well-suited for developing new general or customized prescriptions for treatment of presbyopia and other vision defects. In many embodiments, the techniques of the present invention will make use of adaptive optics systems such as deformable mirrors. Rather than merely using such adaptive optics to measure a patient's ocular aberrations (by configuring the deformable mirror to compensate for aberrations) the adaptive optics system may also be configured to (for example) an aspherical or multi-spherical presbyopia mitigating prescriptive shape. This will allow objective and/or subjective measurements of a candidate prescription by the patient. Objective prescription performance measurements may include imaging of a light spot formed on the retina through the ocular optical system using wavefront or other measurement techniques, ideally using a light spot originating at a plurality of viewing distances (such as a near distance, a far distance, and/or an intermediate distance). Subjective performance evaluation of a candidate prescription may involve displaying a test viewing image (such as a Snellen eye chart, a natural scene or the like) to the eye via an optical path having the adaptive optics system. The patient can then evaluate visual acuity of the test image, ideally at a near viewing distance, a far viewing distance, and/or an intermediate viewing distance. Measurements of pupil sizes and corresponding aberrations at selected viewing conditions (such as selected viewing distances and/or selected brightness) may also be provided, greatly facilitating the derivation of customized presbyopia mitigating prescriptions.

In a first aspect, the invention provides an optical diagnostic device comprising an adjustable viewing target for viewing with a first eye of a patient at a plurality of viewing distances. An adaptive optics system is disposed along an optical path between the first eye and the viewing target. A processor is coupled to the adaptive optics systems and transmits signals thereto. The adaptive optics system assumes a candidate presbyopia-mitigating configuration in response to the signals.

The candidate presbyopia-mitigating configuration may correspond to a candidate aspherical or multifocal refractive correction for the first eye. The adaptive optics system may comprise a deformable mirror and a refractive correction output may be coupled to the processor for outputting the candidate refractive correction. A laser eye surgery system may be coupled to the output so as to allow the laser system to impose the candidate refractive correction on the eye. In some embodiments, the output may be coupled to a contact lens fabrication system, an intraocular lens fabrication system, and/or spectacle lens fabrication system.

An aberrometer may be coupled to the first eye by the optical path. The aberrometer can transmit measured irregular aberration signals to the processor. The processor may determine the signals for transmission to the adaptive optics system in part in response to the measured aberration signals so that the adaptive optics system in the candidate presbyopia-mitigating configuration compensates for aberrations of the eye. A wavefront sensor may be coupled to the optical path, typically for measuring aberrations. Feedback signals may be transmitted from the wavefront sensors to the processor, and the processor may reconfigure the adaptive optics system in response to the feedback signals. The processor may comprise an optimizer which is configured to derive a custom presbyopia-mitigating refractive correction for the first eye. The adjustable viewing target may comprise a wavefront image for wavefront analysis and a verification image for verifying subjective compatibility of the patient with a candidate refractive correction.

The processor may determine accommodation of the eye using a difference between a first low-order aberration measured by the wavefront sensor when the adjustable target has a first viewing distance, and a second low-order aberration measured by the wavefront sensor when the adjustable target has a second viewing distance that is different than the first viewing distance.

Optionally, a measurement device may be oriented to the first eye to transmit a pupil-size signal to the processor. A brightness input may receive brightness commands, and a light exposure of the eye may vary so as to induce the first eye to change from a first pupil size to a second pupil size in response to the brightness command. The brightness input may be coupled to the adjustable target or an ambient light source directed toward the eye. The eye measurement device may comprise a pupilometer, a charge-coupled device (CCD), and/or the like.

In many embodiments, another adaptive optics system may be disposed along another optical path coupled to a second eye. The processor may be coupled to the other adaptive optics system for transmitting candidate presbyopia-mitigating configuration signals thereto so as to allow the patient to evaluate candidate binocular presbyopic mitigation.

In another aspect, the invention provides an optical diagnostic device comprising an adjustable viewing target and an optical path for coupling a first eye of a patient with the viewing target. An input device coupled to the viewing target can adjust at least one of a brightness level or a viewing distance so as to induce changes in a pupil size of a pupil of the first eye between a first pupil size and a second pupil size. A measurement device may be oriented toward the first eye while the first eye views the target. The measurement device transmits a first pupil size signal corresponding to the first pupil size and a second pupil size signal corresponding to the second pupil size.

The viewing target may comprise an adjustable viewing target having a distance viewing configuration, a near viewing configuration, and an intermediate distance viewing configuration. The optical viewing distance along the optical path between the eye and the viewing target in the intermediate configuration may be variable.

An aberrometer may be coupled to the optical path for measuring first aberrations of the eye when the eye is at the first pupil size, and for measuring second aberrations of the eye when the eye is at the second pupil size. A processor coupled to the aberrometer may determine at least one accommodation of the eye from a difference between a first measured aberration of the eye when the adjustable viewing target is at a distance viewing configuration, and a second measured aberration of the eye when the adjustable viewing distance is at a near viewing configuration. The viewing target may comprise an adjustable viewing target having an adjustable viewing brightness level or an adjustable ambient brightness level.

In another aspect, the invention provides an optical diagnostic device for evaluating an eye. The device comprises a viewing target having a first viewing configuration with a first viewing distance and a second viewing configuration with a second viewing distance. The viewing target is coupleable to the eye by an optical path. A wavefront sensor is coupled to the optical path so as to measure a first wavefront when the viewing target is in the first configuration and a second wavefront when the viewing target is in the second configuration. A processor is coupled to the wavefront sensor. The processor determines at least one accommodation of the eye using a difference between the first measured wavefront and the second measured wavefront.

Optionally, a brightness level input may be coupled to at least one of the viewing target or an ambient light source directed toward the eye. The processor may determine a plurality of accommodations at a plurality of lighting conditions.

In another aspect, the invention provides an optical diagnostic method comprising optically coupling a viewing target with a first eye using an adaptive optics system. The adaptive optics system may be configured so as to correspond to a candidate presbyopia-mitigating refractive correction. Performance of the candidate correction may be determined while the viewing target is separated by the eye from a first viewing distance. Presbyopia-mitigating performance of the candidate correction may also be determined while the viewing target is separated from the eye by a second viewing distance. The performance of the eye at the first and second viewing distances may be determined at least in part by measuring a wavefront aberration of the ocular optical system at the first and second viewing distances. The adaptive optics system may be configured to compensate for irregular aberrations of the eye while determining performance of the candidate correction.

In another aspect, the invention provides an optical diagnostic method comprising viewing a target with an eye under a first set of viewing conditions. A first pupil size and a first aberration of the eye are measured under the first viewing conditions. The eye views under a second set of viewing conditions that are different than the first set of viewing conditions so as to induce the eye to change from the first pupil size to a second viewing size. The second pupil size and a second aberration of the eye are measured under the second viewing conditions.

Optionally, a candidate presbyopia-mitigating shape that has been generated in response to the first pupil size, second pupil size, and aberrations of the eye with the first pupil size may be modeled. The target may be viewed with the eye along an optical train which includes the model of the presbyopia-mitigating shape.

The first set of viewing conditions may comprise a first brightness level, and the second set of viewing conditions may comprise a second brightness level that is sufficiently different than the first brightness level to alter pupil dilation. The first set of viewing conditions may comprise a first viewing distance, while the second set of viewing conditions comprises a second viewing distance that is sufficiently different than the first viewing distance to alter pupil dilation.

In another aspect, the invention provides a method comprising measuring an eye while the eye is viewing at a first viewing distance. The eye is measured while the eye is viewing at a second viewing distance, and an accommodation of the eye is determined using a difference between the first measurement at the first viewing distance and the second measurement at the second viewing distance.

The eye measurements may comprise wavefront measurements, and the determining step may comprise identifying a change in low-order aberration. The first viewing distance may comprise a predetermined far-viewing distance, while the second viewing distance may comprise a predetermined near-viewing distance at or beyond an accommodation range of the eye. Accommodation may be determined without fogging of the eye.

BRIEF DESCRIPTION OF THE DRAWINGS

FIG. 7 is a flowchart schematically illustrating measurement of ocular aberrations and/or pupil sizes at a plurality of viewing distances, brightnesses, and the like.

FIG. 8 is a flowchart schematically illustrating a method for deriving and verifying a custom presbyopia-mitigating prescription for a particular patient using the apparatus of FIG. 4.

FIG. 9 schematically illustrates a monocular apparatus for diagnosing and measuring an eye, developing presbyopia-mitigating prescriptions, and the like.

DETAILED DESCRIPTION OF THE INVENTION

The present invention generally provides devices, systems, and methods for diagnosing, measuring, and treating one or both eyes of a patient. The invention allows customized or general presbyopia-mitigating shapes to be developed and improved. The invention also allows accommodation of an eye to be objectively determined, optionally based on measurements of the ocular optics. The invention also allows candidate refractive eye prescriptions to be evaluated objectively and/or subjectively, often without having to fabricate one or more individual test lenses, even when customized prescriptive shapes are to be implemented and evaluated at a plurality of viewing conditions (such as different viewing distances, lighting conditions, and the like). Hence these inventions will find applications for measuring and treating a variety of refractive or other defects of the eye, including presbyopia, spherical errors (including myopia and hyperopia), regular and irregular astigmatism (including high-order aberrations), and the like, and may also find advantageous use for retinal or neural processing disorders such as age-related macular degeneration (AMD), and the like.

Many embodiments of the present invention will make use of adaptive optics systems such as those including a deformable mirror or the like. Adaptive optics systems are well-suited for measuring a patient's ocular aberrations, often by driving the deformable mirror to a configuration which compensates for the overall aberration of the eye. Using an adaptive optics system, the patient may view optometric test targets (such as an eye) chart to test the subjective visual acuity and contrast sensitivity. Optical surfaces for presbyopia correction may be provided by theoretical derivation, optical modeling, empirical clinical trials, or the like, and these presbyopia-mitigating shapes may be verified with the techniques of the present invention to ensure that the patient obtains satisfactory near, intermediate, and distance vision.

Adaptive optics will also facilitate scaling, customization, and optimization of optical surfaces for correction of presbyopia, often without the need for fabricating test lenses or the like. For example, pupil sizes at different target distances and different lighting conditions may be measured. Corresponding residual accommodation may also be measured, either subjectively (for example, by varying a viewing distance and querying the patient so as to determine the accommodation range) or objectively (for example, by measuring ocular optical characteristics while the eye is relaxed or viewing at infinity, and while the eye is attempting to view a near image at or beyond the accommodation range of the patient). The pupil sizes, residual accommodation, and/or the ocular aberrations can be used in deriving or selecting an optimal candidate surface for treatment of presbyopia. The presbyopia-mitigating optical surface will often be combined with the patient's ocular aberrations to configure the adaptive optics system so that a proposed treatment can be subjectively verified by the patient prior to laser eye surgery, fabrication and insertion of an intraocular lens, fabrication of contact lenses or spectacles, and the like.

The present invention can be readily adapted for use with existing laser systems, wavefront measurement systems, and other optical measurement devices. While the systems, software, and methods of the present invention are described primarily in the context of a laser eye surgery system, it should be understood the present invention may be adapted for use in alternative eye treatment procedures and systems such as spectacle lenses, intraocular lenses, contact lenses, corneal ring implants, collagenous corneal tissue thermal remodeling, and the like.

Figure 1:
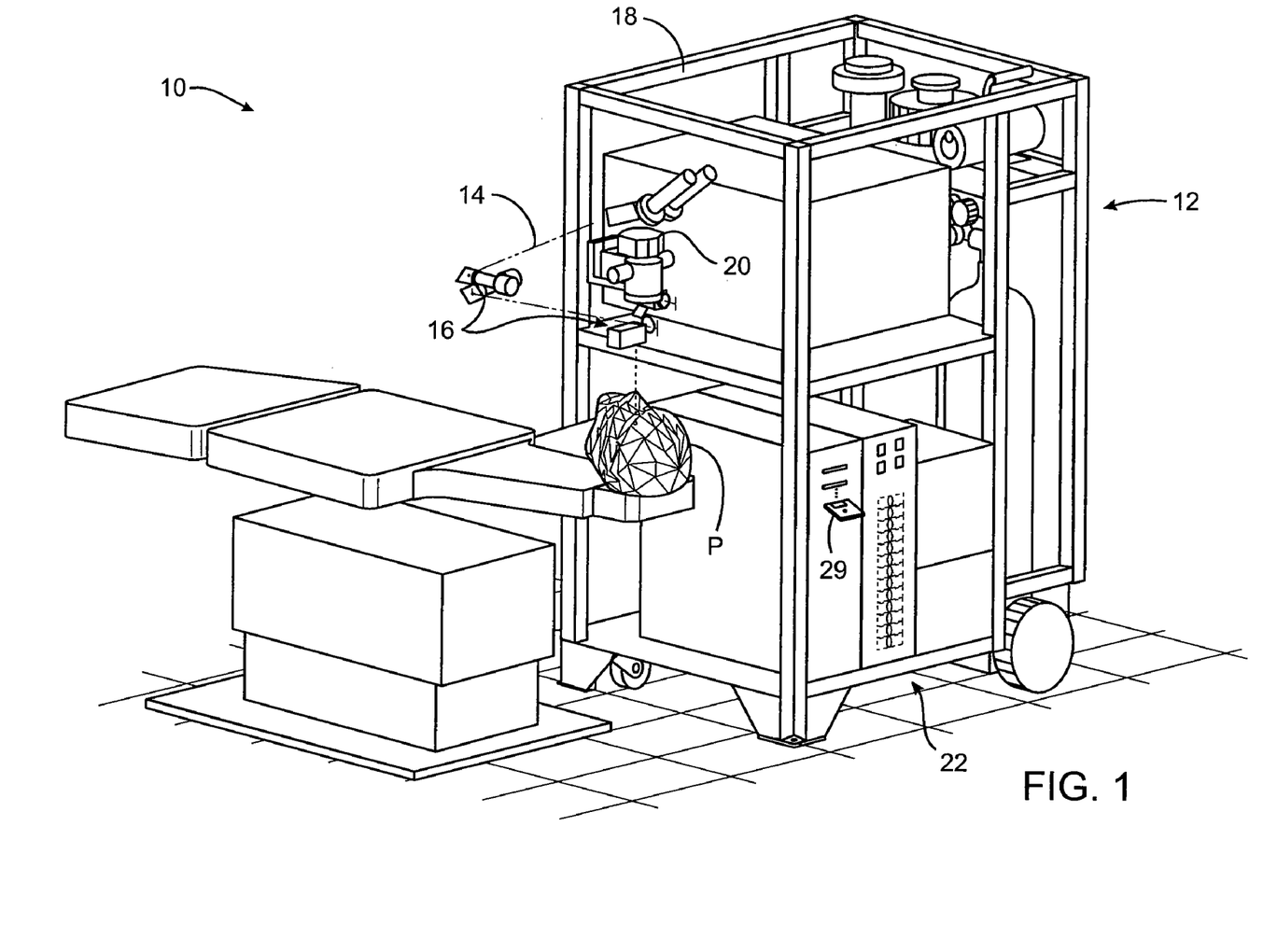
FIG. 1 illustrates a laser ablation system according to an embodiment of the present invention.

Referring now to FIG. 1, a laser eye surgery system 10 of the present invention includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of the eye.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via laser delivery optics 16. The present invention may also be useful with alternative sources of ultraviolet or infrared radiation, particularly those adapted to controllably ablate the corneal tissue without causing significant damage to adjacent and/or underlying tissues of the eye. In alternate embodiments, the laser beam source employs a solid state laser source having a wavelength between 193 and 215 nm as described in U.S. Pat. Nos. 5,520,679 and 5,144,630 to Lin and 5,742,626 to Mead, the full disclosures of which are incorporated herein by reference. In another embodiment, the laser source is an infrared laser as described in U.S. Pat. Nos. 5,782,822 and 6,090,102 to Telfair, the full disclosures of which are incorporated herein by reference. Hence, although an excimer laser is the illustrative source of an ablating beam, other lasers may be used in the present invention.

Laser 12 and laser delivery optics 16 will generally direct laser beam 14 to the eye of patient P under the direction of a computer system 22. Computer system 22 will often selectively adjust laser beam 14 to expose portions of the cornea to the pulses of laser energy so as to effect a predetermined sculpting of the cornea and alter the refractive characteristics of the eye. In many embodiments, both laser 12 and the laser delivery optical system 16 will be under control of computer system 22 to effect the desired laser sculpting process, with the computer system effecting (and optionally modifying) the pattern of laser pulses. The pattern of pulses may be summarized in machine readable data of tangible media 29 in the form of a treatment table, and the treatment table may be adjusted according to feedback input into computer system 22 from an automated image analysis system (or manually input into the processor by a system operator) in response to real-time feedback data provided from an ablation monitoring system feedback system. The laser treatment system 10, and computer system 22 may continue and/or terminate a sculpting treatment in response to the feedback, and may optionally also modify the planned sculpting based at least in part on the feedback.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913; 4,669,466; 4,732,148; 4,770,172; 4,773,414; 5,207,668; 5,108,388; 5,219,343; 5,646,791; and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss Meditec, and the like.

Figure 2:
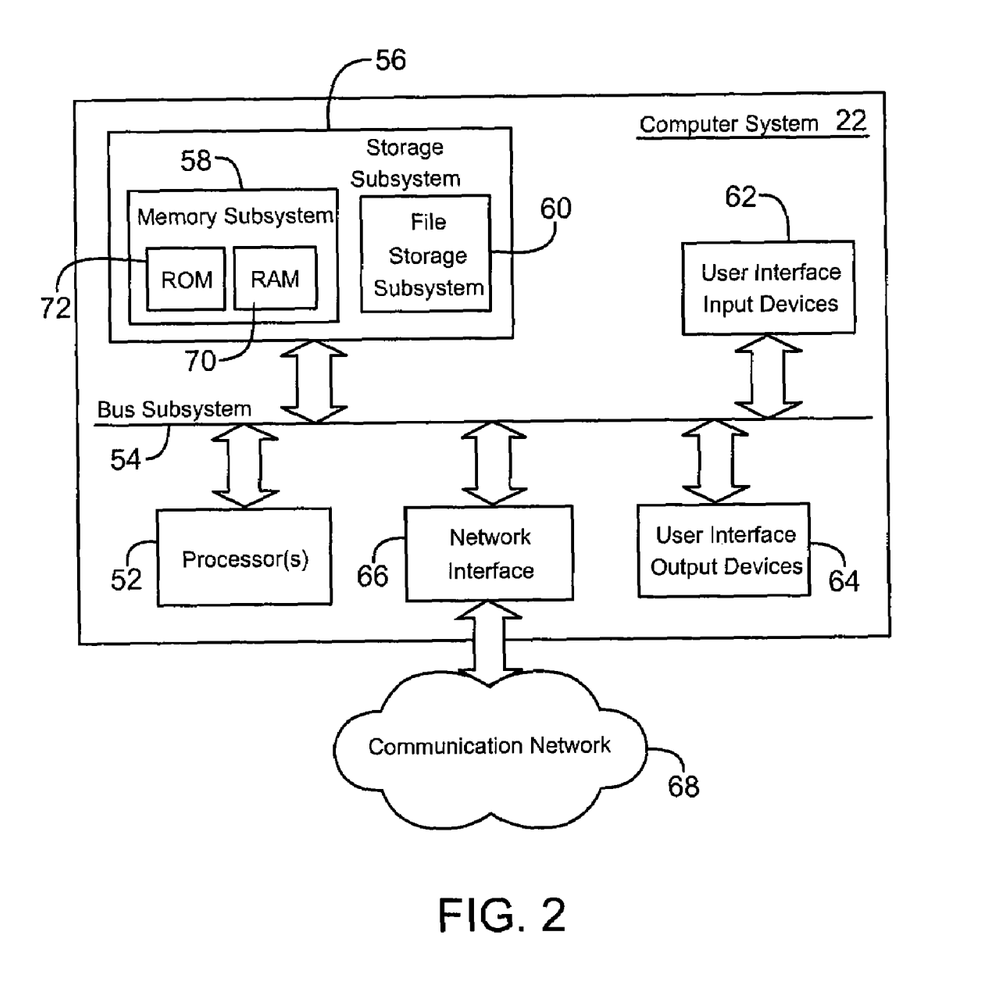
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 stores the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
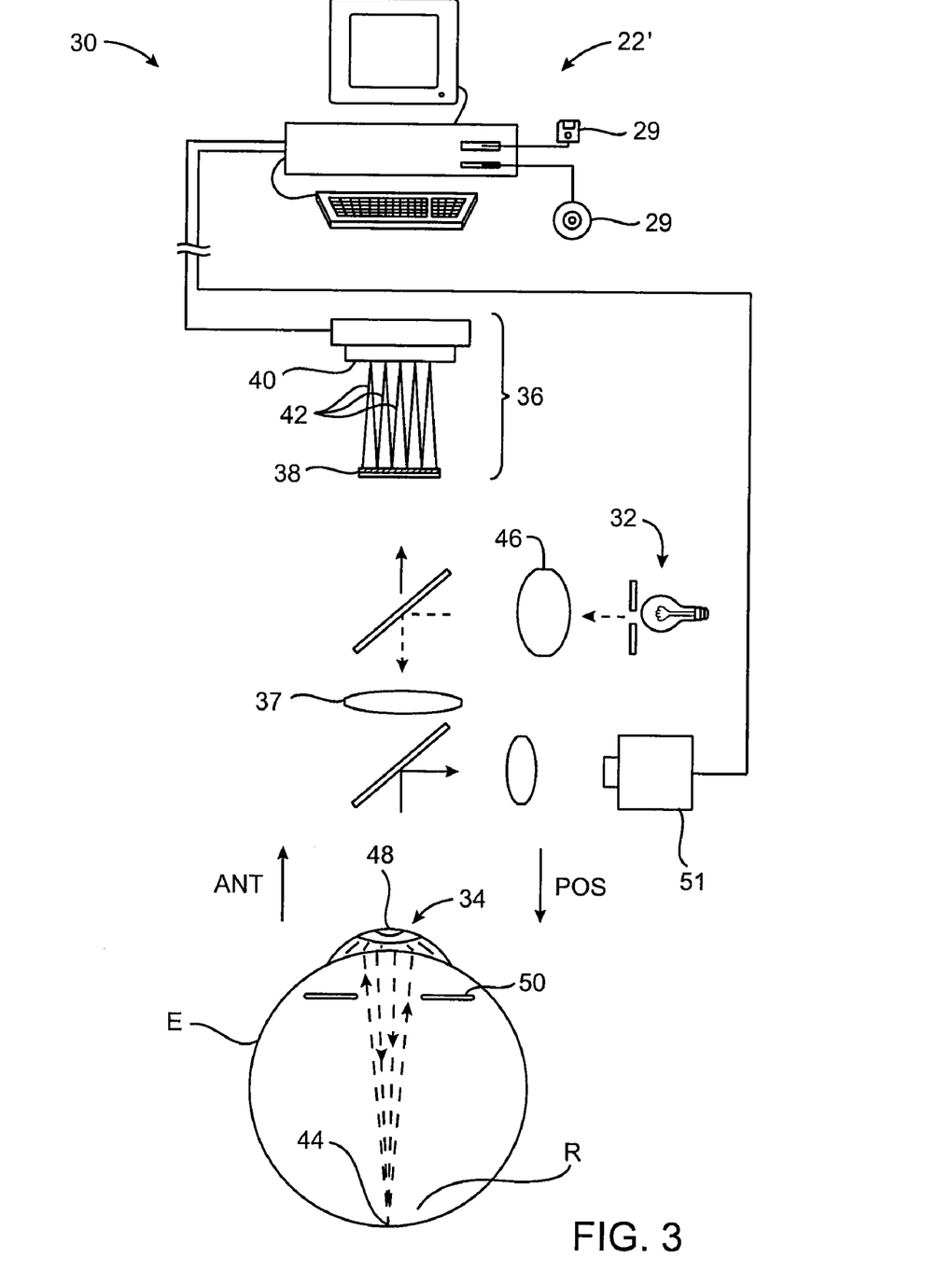
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optics system, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

The wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
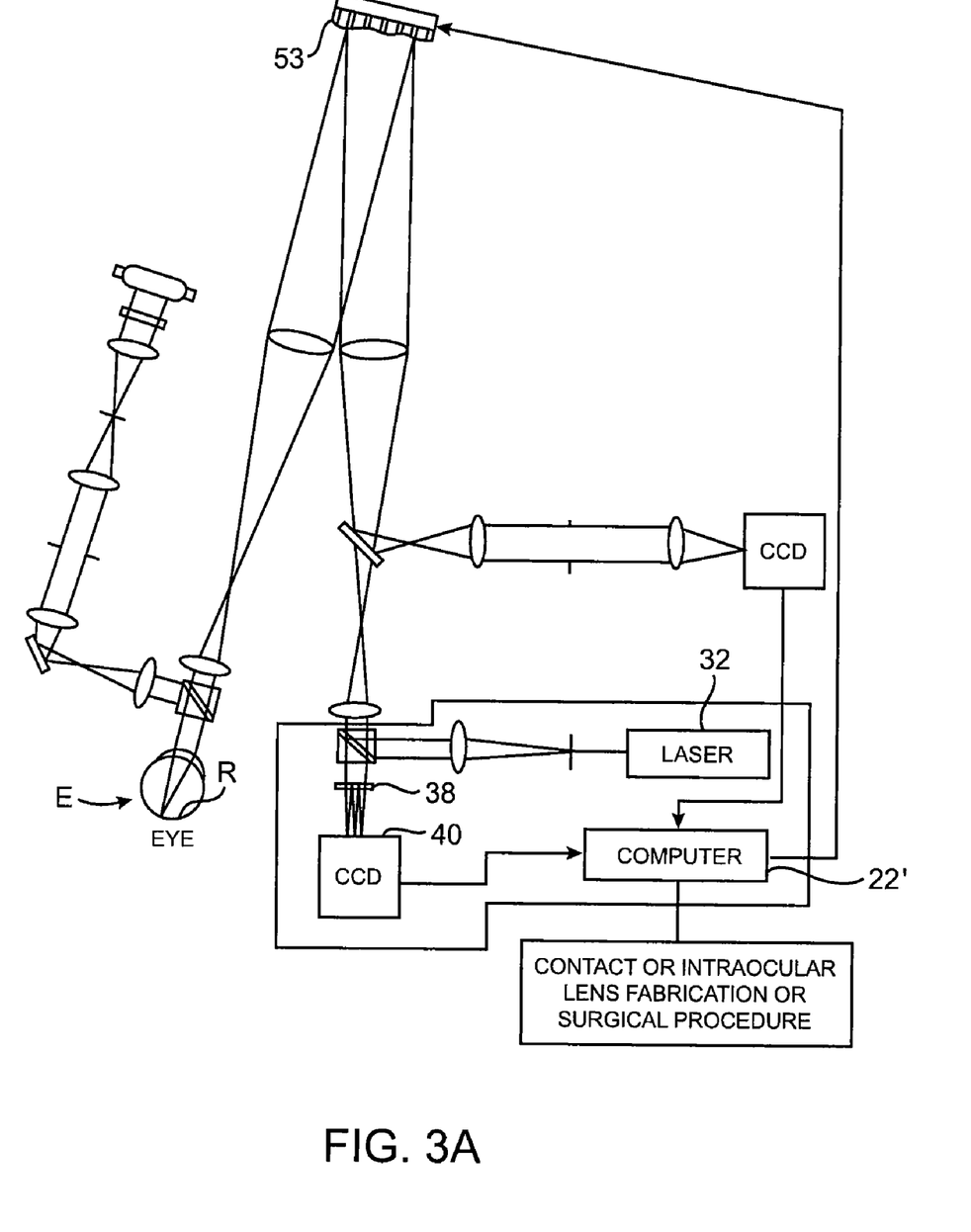
FIG. 3A illustrates another wavefront measurement system according to another embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optics system 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations comprise elements of a VISX WaveScan® system, available from VISX, Incorporated of Santa Clara, Calif. One embodiment includes a WaveScan® system with a deformable mirror as described above. An alternate embodiment of a wavefront measuring system is described in U.S. Pat. No. 6,271,915, the full disclosure of which is incorporated herein by reference.

Figure 4:
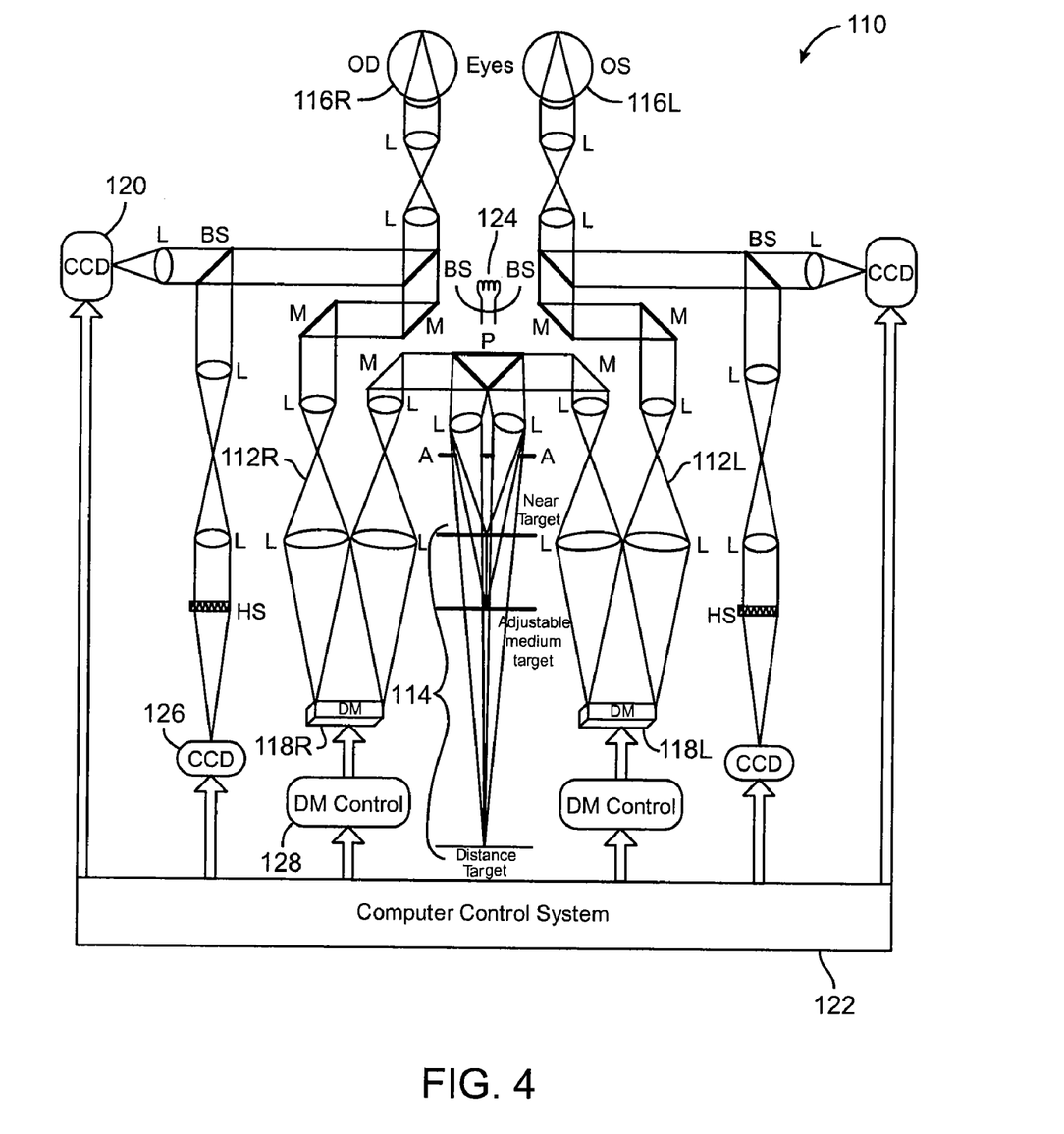
FIG. 4 schematically illustrates a binocular ocular measurement and diagnostic apparatus for measuring accommodation, developing or selecting a presbyopia-mitigating prescription, developing presbyopia-mitigating shapes, and the like, according to the principles of the present invention.

Referring now to FIG. 4, an adaptive optics apparatus 110 generally includes an optical path 112R coupling an adjustable target 114 with a right eye 116R of a patient. A similar optical path 112L couples adjustable target 114 with a left eye 116L, thereby providing a binocular viewing system. As the components of the optical path, sensors, and the like of apparatus 110 along the right optical path 112R are generally similar to those of the left optical path 112L, only the right side need be described to understand the structure and use of the apparatus.

Optical path 112R includes a series of lenses L and mirrors M optically coupling adjustable target 114 to right eye 116R via a deformable mirror 118R. A Hartmann-Shack wavefront sensor HS is coupled to optical path 112R by a beam splitter BS for measurement of aberrations of eye 116R. A sensor 120 is also coupled to the optical path 112R by one or more beam splitters BS for measurement of a size of a pupil of eye 116R, and may also be used to determine a position of the eye and the like, as described above regarding the wavefront measurement system of FIG. 3.

Adjustable target 114 transmits an image along optical path 112R, with the light being profiled by an aperture A having a field stop, the light then being collimated by an adjustable focal-length lens L before being directed along the optical path using a prism P. At the end of the optical path adjacent eye 116R, the light is re-collimated by lenses L to go through the optics of the eye, primarily the cornea and the lens of the eye, so as to form an image on the retina.

When apparatus 110 is used for subjective measurements, light from the retina goes back through the ocular optics and adjacent lenses L of optical path 112R, and is split from the optical path by a first beam splitter BS. This retinal image light is split into two channels by a second beam splitter BS. A first of these two channels is directed by a lens L to sensor 120 for imaging the pupil, the sensor often comprising a charged couple device (CCD), a pupilometer, and/or the like. The second channel is directed from beam splitter BS via adjacent lenses L to Hartmann-Shack wavefront sensor HS.

When the deformable mirror is in a flat configuration, an initial total ocular aberration measurement can be taken of eye 116R, often using adjustable target 114 in a distant viewing configuration. Using this initial measurement, the deformable mirror can be configured to compensate for ocular aberrations. When adjustable target 114 is moved to an intermediate distance, any residual accommodation may kick in. With a near light source, the full residual accommodation of the eye may be employed when the patient tries to focus on the target, particularly if the target is at or beyond the near viewing accommodation of the eye. If the Hartmann-Shack wavefront sensor HS measures the aberration of the eye while the lens of the eye is in its nearest viewing configuration, the total change in the ocular aberration between the distance viewing measurement and the near viewing measurements allows an objective determination of a residual accommodation. Note that the eye can, but need not necessarily be fogged by gradually decreasing the viewing distance to just beyond the accommodation range. Instead, predetermined viewing distances (such as a distance viewing configuration of greater than 8', optionally at about 20'; and a near viewing configuration of less than 5', often being less than 2', and optionally being about 16") may be sufficient for measuring the change in ocular aberration for the eyes of some or all patients, particularly patients at or above a predetermined age (such as over an age of 30, often being over an age of 45).

Adjustable viewing target 114 will often include a light source of visible light such as a light emitting diode (LED), a laser diode, and incandescent or fluorescent bulb, or the like. Optionally, the light source of adjustable target 14 is adjustable in brightness level and/or viewing distance. Adjustable target 114 will typically have an input for varying of the viewing distance and/or brightness level, with the input often being coupled to a computer control system 122. In other embodiments, adjustment of the brightness level or viewing distance may be effected by a manual input, a turret of alternatively selectable lenses, filters, holographic optical elements, or the like. If adjustable target 114 is not under the control of computer control system 122 (by coupling of an input of the adjustable target to a control signal output of the computer system), then the adjustable target will often transmit a signal to a computer so as to indicate the viewing configuration of the target during measurements. In some embodiments, adjustment of the brightness level may be effected using one or more ambient lights 124, with the input for adjusting brightness level optionally being coupled to ambient light 124 and an adjustable brightness light source of target 114, or by using a fixed brightness light source within target 114 in combination with ambient light 124 so as to alter an overall brightness level to eyes 116R, 116L.

Adjustment of the ambient and/or target viewing brightness level allows apparatus 110 to measure pupil size and/or aberrations under different brightness level viewing conditions. As the brightness level of the viewing target or ambient light increases, pupil size decreases. Additionally, as eyes adjust from a near viewing distance to a far viewing distance, pupil size will also often decrease. Apparatus 110 may be used in a room having a low or darkened room lighting to facilitate low brightness level measurements, or a housing or drape may be provided to limit the effect of room lighting on the eye.

Measurement of eyes at a matrix of different viewing conditions will facilitate, customized prescriptions for the patient's eyes. Preferably, pupil measurements and/or aberration measurements will be made at a plurality of viewing conditions, preferably at 3 or more different viewing conditions, ideally at 4 or more viewing conditions. This may facilitate development or selection of presbyopia and other refractive defect mitigating shapes for the eye which are well-suited for typical tasks at multiple viewing conditions. For example, the prescriptive shape may be selected so as to provide good acuity for reading, (often without reading glasses) at a relatively bright, near viewing configuration of the pupil and ocular optics; ideally while also providing good visual acuity for reading signs at a far distance and/or dashboard instruments at an intermediate distance when driving at night; while also maintaining the best available distance viewing acuity under bright-light conditions. Hence, more than one accommodation of each eye 116R, 116L may be measured so as to indicate the adjustability of the lens and other ocular optics of the eye at different lighting conditions.

Adjustable target 114 will often be configured so as to provide three types of viewing distances: near viewing (typically at less than about 2 feet, often at about 16 inches), distant viewing (typically at greater than about 5 feet, often at about 8 feet or more, optionally at 10 feet or more, and in some embodiments at about 20 feet or more), and an intermediate or medium viewing distance. The intermediate viewing distance may be adjustable to a plurality of different settings or throughout a range. The intermediate viewing distance of adjustable target 114 will often be adjustable within a range of about 2 to about 8 feet, often being adjustable within a range from about 32 inches to about 5 feet. Actual linear distance along optical path 112R between eye 116R and adjustable target 114 need not necessarily correspond with the optical viewing distance, as lenses L, mirrors M, or other optical elements may be used to adjust the optical viewing distance. Hence, the light source and field stop of adjustable target 114 may remain the same distance apart throughout the near, intermediate, and distance viewing configurations using a zoom lens arrangement, selectable turret, or the like.

Adjustable target 114 may have a plurality of target images. To facilitate wavefront measurements, adjustable target 114 may include a spot target image projecting a spot of light on the retina of eyes 116R, 116L. The spot light image may then be used by Hartmann-Shack sensor HS together with its associated image capture device such as a CCD 126 and a related analysis module of computer 122 for measuring wavefront aberrations, as described above. Hence, this image may comprise an aberration measurement image. Along with an aberration measurement image, adjustable target 114 may also include any of a wide variety of verification test image shapes such as one or more letters of a Snellen eye chart, a landscape image (particularly for distance viewing), a portrait image (such as for intermediate viewing) small text or detail image (for example, for verifying near visual acuity) and the like.

As visual performance may depend on alignment of eye 116R, deformable mirror 118R, and the verification image existing visual evaluation images may be modified. Specifically, rather than having the eye scan the various lines of letters in the Snellen eye chart at adjustable target 114 (and thereby moving into and out of alignment with the deformable mirror 118R), the eye chart may move or only one letter of the eye chart may be shown at a time. This may help the deformable mirror to accurately compensate for high-order aberration of the eye, as well as maintaining an aspherical or multifocal candidate presbyopia-mitigating shape modeled by deformable mirror 118R at desired axial alignment with the eye, and/or the like.

A number of different deformable mirrors or active mirrors may be used, including first or second generation membrane or foil mirrors, microchip mirrors having 100,000 or more facets, and the like. In the exemplary embodiment, deformable mirror 118R may comprise a system such as that available commercially from Xinetics, Inc. located at Devens, Mass. Alternative deformable mirrors may be available commercially from Boston Micromechines, located at Watertown, Mass., or from FRAUNHOPER-INSTITUTE FOR PHOTONIC MICROSYSTEMS, of Dresden, Germany. Rather than using a deformable mirror, other forms of adaptive optics may also be employed.

The CCD of sensor 120 may include or be coupled to image analysis software and/or hardware so as to allow sensor 120 to measure a size of the pupil of the eye. Commercially available pupilometers may also be employed, including those available from PROCYON INSTRUMENTS, LTD. under model numbers P2000SA and P3000 located in the United Kingdom. Processing hardware and/or software modules such as image analysis software of sensor 120 may generally be resident in a processor of the associated sensor or CCD, in computer control system 122, or an intermediate processor coupling a sensor or controller to the elements of system 10 in a wide variety of alternative centralized or distributed data processing architectures.

Deformable mirror controller 128 can change the surface of deformable mirror 118R quite arbitrarily, so that is possible to create a surface of the deformable mirror which corresponds to and/or model a variety of candidate presbyopia-mitigating refractive shapes. Additionally, a deformable mirror can compensate for ocular aberrations of the eye as described above regarding FIG. 3A. Advantageously, controller 128 can configure deformable mirror 118R to combine an ocular aberration compensator with the candidate presbyopia-mitigating shape. When such a shape is applied to deformable mirror 1118R, the patient will undergo an effect which is similar to the proposed treatment of the eye such as customized laser eye surgery, an intraocular lens, a contact lens, or the like. By configuring adjustable target 114 to a variety of different target distances and brightness levels, visual acuity and contrast sensitivity can be measured to examine the effectiveness of the overall proposed refractive correction for treatment of presbyopia. This allows the wavefront measurements to be used as a feedback signal, such as for reconfiguring the deformable mirror (and the corresponding candidate prescription). Processor 122 may include, for example, an optimizer module for deriving subsequent deformable mirror configurations. Suitable optimizer modules may comprise software and/or hardware configured for optimizing a deformable mirror shape using a Downhill Simplex method, a direction set method, a simulated annealing method, and/or the like. In the binocular system of 110, similar adjustments can be made to deformable mirror 118L to compensate for aberrations of the eye 116L, and to model a presbyopia-mitigating shape. The presbyopia-mitigating shape of the left eye may be the same as or different than that of the right eye. For example, where the left eye has a greater residual accommodation than the right eye, the strength of a candidate presbyopia-mitigating shape may be reduced as compared to that other eye. Furthermore, the binocular system of FIG. 4 allows the patient to determine acceptability of monovision systems which rely on one eye primarily for distance and the other eye for near viewing, and hybrid systems which use one approach (such as a central add region) for one eye and a different approach (such as peripheral add region) for the other eye to mitigate presbyopia (for example, see U.S. patent application Ser. No. 10/849,573, titled *Binocular Optical Treatment For Presbyopia*, filed on May 18, 2004, the full disclosure of which is incorporated herein by reference).

Figure 5:
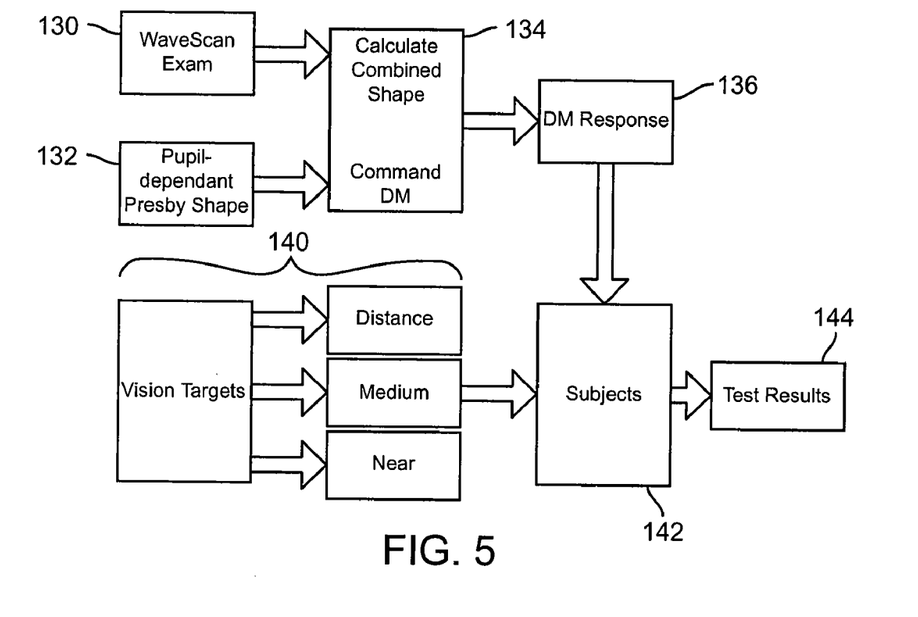
FIG. 5 schematically illustrates a system block diagram for a presbyopia-mitigating prescription verification system using the apparatus of FIG. 4.

Referring to FIG. 5, the apparatus of FIG. 4 can be used to test and verify effectiveness of a candidate presbyopia shape. The patient may initially undergo a wavefront examination, optionally using Wavescan® sensors commercially available from VISX, Incorporated, using the apparatus of FIG. 4, using the apparatus of FIG. 3, or the like, in block 130. Aberration measurement and/or wavefront error data is recorded and transmitted to computer 122 (see FIG. 4). An initial presbyopia shape 132 is also input into the computer, with the initial shape preferably being determined from at least one measurement of the pupil as described in copending U.S. patent application Ser. No. 10/738,358, filed Dec. 5, 2003, and entitled *Presbyopia Correction Using Patient Data*, the full disclosure of which is incorporated herein by reference. The presbyopia-mitigating shape and aberration data are used to calculate a combined presbyopia-mitigating and aberration-mitigating shape for use by the deformable mirror control 128 of computer 122 at block 134. Signals are sent to the deformable mirror which assumes the desired shape, with the signals optionally being adjusted relative to the deformable mirror response so as to accurately model a candidate prescription at block 136.

One or more vision targets at different viewing conditions (for example, having differing contrast, at differing viewing distances, at differing brightness levels, and/or the like) are used to form a testing matrix in blocks 140. These targets are presented to the patient via the apparatus of FIG. 4 in step 142, with visual acuity and contrast sensitivity being recorded, ideally along with subjective satisfaction scores, as a verification measurement 144. Optionally, if the verification indicates that the candidate prescription provides the desired result, the prescription may be employed for treatment of the patient.

Figure 6:
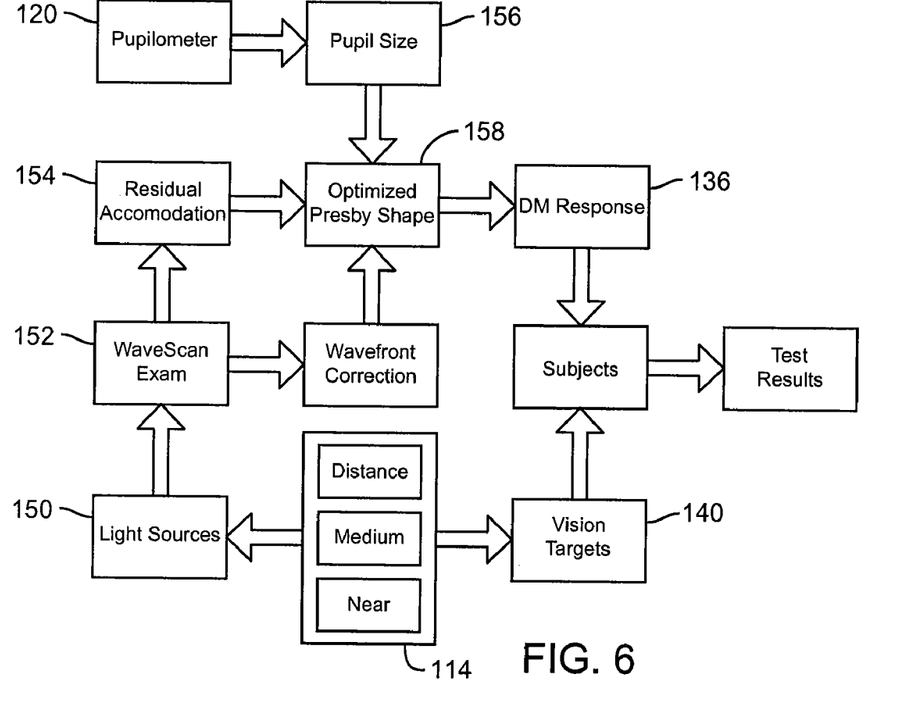
FIG. 6 schematically illustrates a system block diagram for presbyopia optimization and verification using the apparatus of FIG. 4.

Referring now to FIG. 6, the apparatus of FIG. 4 may be employed to select, derive, and/or optimize a customized presbyopia-mitigating treatment for patient. The patient's ocular aberrations may be measured using a measurement image such as a light spot aperture in block 150. For example, ocular aberrations may be measured using such a measurement image at a distance viewing configuration so as to provide a wavefront aberration at block 152. A separate wavefront measurement may then be taken with adjustable target 114 in a near viewing configuration, and the difference between these measurements used to determine residual accommodation 154. More specifically, residual accommodation will generally be calculated from the differences in low-order aberration (particularly the difference in spherical power) of the ocular optics when the eye is focusing at a distant image and at a near image. An integrated or separate pupilometer such as sensor 120 can be used to measure the pupil size at different lighting conditions, and at different viewing distances or vergence conditions in step 156. The information from the wavefront measurements, residual accommodation calculations, and pupil measurements may be used to derive a candidate presbyopia-mitigating shape in block 158. Specific methodology for calculating the presbyopia-mitigating shape are described in more detail in copending application Ser. No. 10/738,358, previously incorporated herein by reference.

Advantageously, once a candidate presbyopia-mitigating shape has been identified it may be mapped onto the deformable mirror in block 136. As can be understood with reference to FIG. 4, spot illumination of the eye via the deformable mirror may provide feedback on the effectiveness at near, distant, and medium viewing distances, thereby allowing further refinements to the candidate prescription. Once such objective tests have established an appropriate candidate prescription, a matrix of subjective visual acuity targets 140 may be presented to the patient so as to determine overall performance of the proposed treatment.

Figures 7, 8:
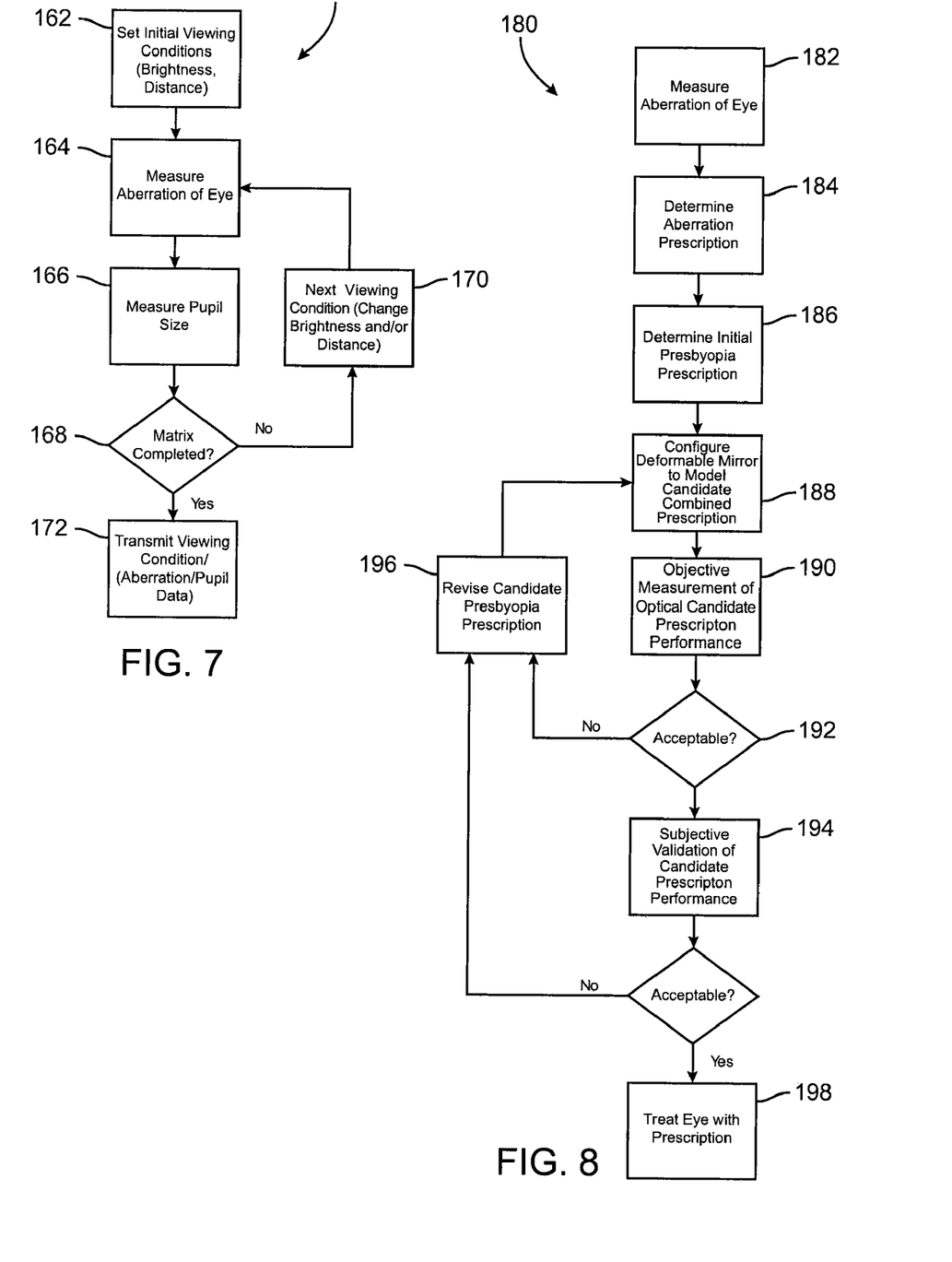

Referring now to FIG. 7, a flowchart schematically illustrates a method 160 for measuring aberration of the eye and pupil sizes at a plurality of viewing conditions. Using the apparatus of FIG. 4, a variety of differing viewing distances, brightness conditions, and/or images may be employed. In many embodiments, initial viewing conditions will be set 162 by selecting one or more appropriate viewing distance, brightness level, image contrast, image type, and the like. Aberration of the eye will be measured 164, and pupil size measurements 166 will be taken. The pupil size measurements 166 will often be taken simultaneously with aberration eye measurements at the viewing conditions, although they may also be taken at least partially before and/or after the aberration eye measurements. If the desired matrix of viewing conditions has not yet been completed 168, the next desired viewing conditions may then be implemented, for example, using apparatus 110 of FIG. 4. Aberrations and/or pupil size measurements 164, 166 may then be taken at the new viewing condition, with the viewing condition revised and additional measurements taken until the desired matrix of measurements has been completed. The aberration and pupil data at the various measurement matrix conditions may then be transmitted in step 172.

The matrix of desired viewing conditions may comprise one or more of the following conditions: focusing on a near image, focusing a distant image under photopic conditions, under mesopic conditions, under scotopic conditions, focusing at an intermediate object, and the like. In many embodiments, the matrix of desired viewing conditions may be predetermined before initial measurements are taken. In other embodiments, the matrix may vary depending on measurement results. In some embodiments, the order of measurements may be determined so as to avoid excessive delays when the eye adjusts. Selected measurements may be avoided, for example, one, some, or all aberration measurements of the eye may not be needed so that the apparatus measures at least two sequential pupil sizes without an aberration eye measurement.

FIG. 8 schematically illustrates a method 180 for deriving and verifying a presbyopia-mitigating prescription shape using the apparatus of FIG. 4. Measurement of eye aberration 182 may be taken, optionally using the method of FIG. 7. An aberration prescription is determined 184 and an initial presbyopia prescription is provided 186. The aberration prescription and/or presbyopia prescription will often be selected at least in part based on the measurements of the eye in step 182. The aberration prescription may be determined using methods developed for known wavefront sensor systems. Similarly, an initial presbyopia prescription may be selected from known or proposed presbyopia-mitigating shapes, including those that have been described for use in laser eye surgery, intraocular lenses, contact lenses, or the like. Such presbyopia-mitigating shapes often include axisymmetric or asymmetric shapes, multi-focal shapes, and may also include aspheric shapes. The initial presbyopia prescription may be scaled, including both the power and the size of the presbyopia-mitigating shape, based at least in part on measurements of the eye taken in step 182 or previously, including pupil size measurements, residual accommodation measurements, and the like.

The deformable mirror is configured to model a candidate combined prescription 188, with the combined prescription reflecting both the aberration prescription and the presbyopia prescription. Objective measurements of the optical candidate prescription performance 190 are taken using a method similar to that shown in FIG. 7, and if performance is not acceptable 192, the candidate prescription is revised 194, and the mirror reconfigured 188. Revising of the candidate prescription 194 may comprise, for example, increasing a scale of the presbyopia prescription, changing of power of the presbyopia prescription, selecting a different presbyopia-mitigating shape, implementing a change-vector in a multi-dimensional optimization of the presbyopia-mitigating shape, the aberration-mitigating shape, and/or the combined prescription, and the like.

While subjective viewing images may be employed for measurement 182, 190, the method 180 will often employ a wavefront measurement image to generate a small spot on the retina or the like. Once objective measurements of the prescription performance are acceptable, subjective validation 194 may be implemented using one or more viewing images. The viewing images may change depending on the viewing configurations, so that subjective performance validation may employ a method similar to that illustrated in FIG. 7, but may include a subjective evaluation by the patient in place of (or in addition to) the aberration measurement step 164. For example, the viewing image may simulate newsprint for near viewing conditions under medium lighting, and may simulate a natural landscape for bright lighting conditions at far distance. If this subjective validation indicates that the prescription is not acceptable, the prescription may be revised 196 and subjective and/or objective evaluations may be repeated until subjective and/or objective evaluation criteria are met. The eye may then be treated 198 with the validated prescription.

Using the binocular system of FIG. 4, the presbyopia-mitigating prescription for each eye of a patient may be derived, scaled, selected and/or optimized independently, with testing optionally being performed so as to provide the desired performance when both eyes are used together for stereovision throughout a range of viewing conditions.

The devices and methods described herein may have a variety of advantages. For example, changes in high-order aberrations at differing viewing conditions (such as changing between a distant viewing configuration and a near viewing configuration) may be very useful in shape optimization for treating presbyopia and other viewing conditions. LASIK flap and healing and other healing effects may be use to change the presbyopia-mitigating shape. Additional changes in high-order aberrations associated with refocusing of the crystalline lens may similarly be the basis for adjusting a presbyopia-mitigating shape. Hence, along with using differences in low-order aberrations to determine residual accommodation, there will also be advantageous applications for differences in high-order aberrations in shape optimization.

Figure 9:
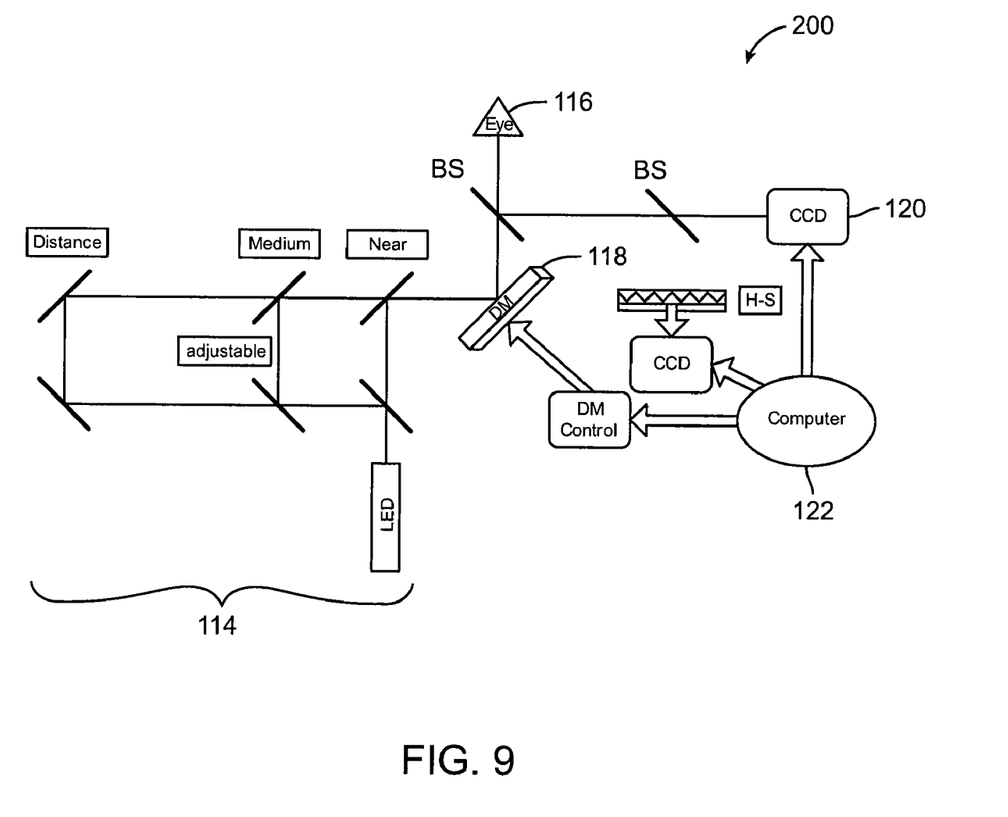

FIG. 9 schematically illustrates an alternative presbyopia-mitigating apparatus 200 having many of the features described above regarding the apparatus of FIG. 4. This embodiment includes only a monocular configuration, so that reference numbers are not differentiated between right and left optical paths.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. An optical diagnostic device for use with a first eye of a patient, the first eye of the patient having a refractive defect, the optical diagnostic device comprising:
    an adjustable viewing target for viewing with the first eye of the patient at a plurality of viewing distances including a first viewing distance and a second viewing distance;
    an adaptive optics system disposed along an optical path between the first eye and the viewing target; and
    a processor coupled to the adaptive optics system so as to transmit signals thereto, the adaptive optics system assuming a candidate prescription configuration in response to the signals such that the adaptive optics system is in the candidate prescription configuration when the adjustable viewing target is at the first viewing distance and when the adjustable viewing target is at the second viewing distance so as to verify the candidate prescription is acceptable for mitigation of the refractive defect with the first eye at the plurality of viewing distances.

2. The optical diagnostic device of claim 1, wherein the candidate prescription configuration corresponds to a candidate refractive correction for the first eye.

3. The optical diagnostic device of claim 1, further comprising a prescription output coupled to the processor for outputting the candidate prescription configuration.

4. The optical diagnostic device of claim 3, further comprising a laser eye surgery system coupled to the prescription output so as to allow the laser system to impose the candidate prescription configuration on the first eye.

5. The optical diagnostic device of claim 3, wherein the prescription output is coupled to at least one of:
    a contact lens fabrication system,
    an intraocular lens fabrication system, and
    a spectacle lens fabrication system.

6. An optical diagnostic device for use with a first eye of a patient, the first eye of the patient having a refractive defect, the optical diagnostic device comprising:
    an adjustable viewing target for viewing with a first eye of a patient at a plurality of viewing distances including a first distance and a second distance;
    an adaptive optics system disposed along an optical path between the first eye and the viewing target; and
    a processor coupled to the adaptive optics system and transmitting signals thereto, the adaptive optics system assuming a candidate viewing defect-mitigating configuration in response to the signals so as to allow the patient to subjectively evaluate mitigation of the refractive defect of the first eye provided by the candidate viewing defect-mitigating configuration at the plurality of viewing distances.

7. The optical diagnostic device of claim 6, wherein the candidate viewing defect-mitigating configuration comprises an aspherical or multifocal shape configuration suitable for mitigating a viewing defect.

8. The optical diagnostic device of claim 6, wherein the adjustable viewing target defines three target viewing distances, where two target viewing distances are fixed and a third target viewing distance is adjustably disposed between the fixed target viewing distances.

9. An optical diagnostic device comprising:
   an adjustable viewing target for viewing with a first eye of a patient at a plurality of viewing distances;
   an adaptive optics system disposed along an optical path between the first eye and the viewing target;
   a processor coupled to the adaptive optics system and transmitting signals thereto, the adaptive optics system assuming a candidate prescription configuration in response to the signals; and
   a measurement device oriented toward the first eye, wherein the measurement device transmits a pupil size signal to the processor, and wherein the processor determines the candidate prescription configuration in response to the pupil size signal.

10. The optical diagnostic device of claim 9, further comprising a brightness level input for receiving brightness level commands, a light exposure of the eye varying so as to induce the first eye to change from a first pupil size to a second pupil size in response to the brightness level commands.

11. The optical diagnostic device of claim 10, wherein the brightness level input is coupled to at least one of the adjustable viewing target and an ambient light source directed toward the first eye.

12. An optical diagnostic device comprising:
   an adjustable viewing target for viewing with a first eye of a patient at a plurality of viewing distances including a first viewing distance and a second viewing distance;
   an adaptive optics system disposed along an optical path between the first eye and the viewing target; and
   a processor coupled to the adaptive optics system and transmitting signals thereto, wherein the adaptive optics system assumes a candidate prescription configuration in accordance with a prescription to be evaluated so as to generate feedback signals, and wherein the processor modifies the adaptive optics system from the candidate prescription configuration to a revised candidate prescription configuration in response to the feedback signals generated while the adaptive optics system is in the candidate prescription configuration and the first eye views the adjustable viewing target at the first viewing distance and the second viewing distance.

* * * * *